United States Patent [19]

Matsumoto et al.

[11] Patent Number: 4,558,143

[45] Date of Patent: Dec. 10, 1985

[54] PROCESS FOR PREPARING 4-OXO-4,5,6,7-TETRAHYDROBENZOFURAN

[75] Inventors: Masakatsu Matsumoto, Sagamihara; Nobuko Watanabe, Kamakura, both of Japan

[73] Assignee: Sagami Chemical Research Center, Tokyo, Japan

[21] Appl. No.: 520,519

[22] Filed: Aug. 4, 1983

[30] Foreign Application Priority Data

Aug. 6, 1982 [JP] Japan ................................ 57-136231

[51] Int. Cl.$^4$ ........................................... C07D 307/79
[52] U.S. Cl. .................................................. 549/471
[58] Field of Search .......................................... 549/471

[56] References Cited

PUBLICATIONS

Besagni et al., Bull. Soc. Chim. France, pp. 4041–4047 (1971).

*Primary Examiner*—Henry R. Jiles
*Assistant Examiner*—Bernard I. Dentz
*Attorney, Agent, or Firm*—Antonelli, Terry & Wands

[57] ABSTRACT

A 4-oxo-4,5,6,7-tetrahydrobenzofuran derivative is prepared by reacting a 1,3-cyclohexanedione derivative with chloroacetaldehyde in the presence of a base while maintaining the reaction mixture at a pH of from 4 to 10, and treating the reaction mixture with an acid. The 4-oxo-4,5,6,7-tetrahydrobenzofuran derivatives are useful as an intermediate for synthesis of various kinds of drugs.

1 Claim, No Drawings

PROCESS FOR PREPARING 4-OXO-4,5,6,7-TETRAHYDROBENZOFURAN

BACKGROUND OF THE INVENTION

The present invention relates to a process for preparing 4-oxo-4,5,6,7-tetrahydrobenzofuran derivatives. More specifically, the present invention relates to a process for preparing 4-oxo-4,5,6,7-tetrahydrobenzofuran derivatives of the formula (I):

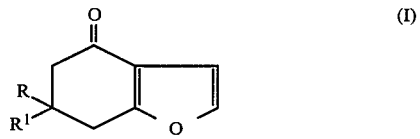

wherein R and R¹ are hydrogen atom or an alkyl group.

The benzofuran derivatives of the formula (I) are useful as an intermediate for synthesis of drugs, particularly as an intermediate for synthesis of 4-hydroxyindole which is a key intermediate for synthesis of Pindolol, or as an intermediate for synthesis of various kinds of 4-substituted indole drugs (K. Saemeli: Helv. Physiol. Acta, 25, 221(1967); Japanese Patent Unexamined Publication No. 103160/1981).

As a process for preparing 4-oxo-4,5,6,7-tetrahydrobenzofuran derivatives, there hitherto has been known Feist-Benary synthesis. That is, a process in which 1,3-cyclohexanedione is condensed with chloroacetoaldehyde in the presence of a base (E. Bisagni et al.: Bull. Soc. Chim. Fr., 4041(1971)). The abovementioned method, however, is not suitable for the industrial production because of low yield of the desired 4-oxo-4,5,6,7-tetrahydrobenzofuran derivative, as is utmost about 40%.

It is an object of the present invention to provide a process for preparing 4-oxo-4,5,6,7-tetrahydrobenzofuran derivatives.

Another object of the present invention is to provide a process in which 4-oxo-4,5,6,7-tetrahydrobenzofuran derivatives can be easily prepared in a high yield by condensing a 1,3-cyclohexanedione derivative with chloroacetoaldehyde.

SUMMARY OF THE INVENTION

It has now been found that it is important to adjust the reaction condition for condensing a 1,3-cyclohexanedione derivative and chloroacetoaldehyde so as to maintain the balance between the desired reaction and the dissociation equilibrium between the polymer and monomer of chloroacetaldehyde in order to apply the Feist-Benary synthesis to the above reaction, since chloroacetaldehyde is relatively hard to exist in the reaction mixture as a monomer. In fact, when the reaction is conducted under a considerably strong acidic condition (1,3-cyclohexanedione derivative and chloroacetaldehyde being strong acids) or a strong basic condition, a condensed product of two moles of 1,3-cyclohexanedione derivative and one mole of chloroacetaldehyde is produced in a considerably large amount. Particularly, under a strong basic condition, a polymer of cyclohexanedione which is partially dehydrochlorinated is produced.

In accordance with the present invention, there can be provided a process for preparing a 4-oxo-4,5,6,7-tetrahydrobenzofuran derivative of the formula (I):

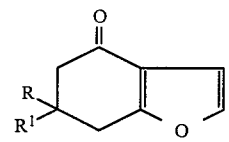

wherein R and R¹ are hydrogen atom or an alkyl group, by reacting a 1,3-cyclohexanedione derivative of the formula (II):

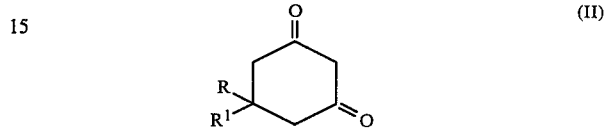

wherein R and R¹ are as defined above, with chloroacetaldehyde in the presence of a base while maintaining at a pH of from 4 to 10, and then treating the reaction mixture with an acid. The reaction efficiency is poor at a pH of less than 4 and more than 10.

DETAILED DESCRIPTION

Both the 1,3-cyclohexanedione derivatives of the formula (II) and chloroacetaldehyde being the starting materials of the present invention can be easily obtained by industrial processes.

The process of the present invention is essentially carried out in the presence of a base. Examples of the base are, for instance, the basic alkali metal salts such as lithium hydroxide, sodium hydroxide, potassium hydroxide, lithium carbonate, sodium carbonate, potassium carbonate, lithium hydrogencarbonate, sodium hydrogencarbonate, potassium hydrogencarbonate, and the organic bases such as pyridine and triethylamine. The base is generally employed in an equimolar amount of slightly excess amount to the used 1,3-cyclohexanedione derivative of the formula (II).

Though the process of the present invention is preferably carried out in water for smoothly proceeding the reaction, an organic solvent such as ethyl acetate, dichloromethane or toluene can be used in combination with water when the reaction materials and the product are slightly soluble in water. The use of an alcoholic solvent such as methanol having a nucleophilicity is not suitable because such a solvent causes a side reaction.

The reaction is easily proceeded at a temperature of from −20° to 100° C., preferably from −10° C. to a room temperature for producing the desired compound in good efficiency.

After completion of the condensing reaction of a 1,3-cyclohexanedione derivative and chloroacetaldehyde, it is necessary to treat the reaction mixture with an acid for dehydrating the following compound (IV), because the reaction is terminated at the following step under the above reaction conditions:

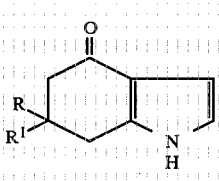

wherein R and $R^1$ are as defined above.

Examples of the acid are, for instance, inorganic acids such as sulfuric acid, hydrochloric acid, organic acids such as sulfonic acid, which are usually utilized in the dehydration reaction.

The compound (I) can be easily converted into a 4-oxo-4,5,6,7,-tetrahydroindole derivative of the formula;

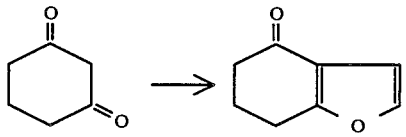

by reacting with ammonia.

The present invention is more specifically described and explained by means of the following Examples and Reference Example, in which all % are by weight unless otherwise noted. The Reference Example is to illustrate the preparation of 4-oxo-4,5,6,7-tetrahydroindole from 4-oxo-4,5,6,7-tetrahydrobenzofuran. It is to be understood that the present invention is not limited to the Examples, and various changes and modifications may be made in the invention without departing from the spirit and scope thereof.

EXAMPLES 1 to 9 AND COMPARATIVE EXAMPLES 1 to 4

To 5 ml of water were added 1.12 g (10 mmoles) of 1,3-cyclohexanedione and the each base shown in Table 1, and then 2 ml of 40% aqueous solution of chloroacetaldehyde was added thereto. The resulting mixture was stirred at a room temperature for 2 hours. To the reaction mixture was added about 10 ml of ethyl acetate, and then the reaction mixture was acidified with 0.5 to 1 ml of sulfuric acid and stirred for 30 minutes. The resulting ethyl acetate layer was analyzed by gas-liquid chromatography (hereinafter referred to as "GLC") (SE30 10%, 1.2 m×3 mmφ glass column, 130° C.) using p-dimethoxybenzene as an internal standard. The obtained each result is shown in Table 1. It was proved from the results of the GLC that 4-oxo-4,5,6,7-tetrahydrobenzofuran was produced in a yield shown in Table 1, in each Example. Comparative Example 1 was carried out in the absence of a base.

TABLE 1

| | Base (mmole) | pH of the reaction mixture Start | End | Yield (%) |
|---|---|---|---|---|
| Com. Ex. 1 | none | <1 | <1 | 7 |
| Com. Ex. 2 | NaOH (5) | 1.4 | 0.9 | 26 |
| Ex. 1 | CaCO$_3$ (6) | 4.3 | 5.9 | 36 |
| Ex. 2 | CH$_3$CO$_2$Na (12) | 4.4 | 4.2 | 41 |
| Ex. 3 | Pyridine (12) | 4.5 | 4.8 | 44 |
| Ex. 4 | Triethylamine (12) | 5.4 | 5.5 | 58 |
| Ex. 5 | NaHCO$_3$ (12) | 5.8 | 6.2 | 61 |
| Ex. 6 | Ba(OH)$_2$ (6) | 6.0 | 6.2 | 48 |
| Ex. 7 | NaOH (10) | 7.6 | 7.6 | 66 |
| Ex. 8 | NaOH* | 8.2 | 7.7 | 64 |
| Ex. 9 | NaOH* | 10 | 8.9 | 56 |
| Com. Ex. 3 | Ca(OH)$_2$ (10) | 11.6 | 10.8 | 30 |
| Com. Ex. 4 | NaOH* | 12 | 9.8 | 19 |

*The pH was adjusted with 2N NaOH solution.

EXAMPLE 10

To a mixture of 1.12 g (10 mmoles) of 1,3-cyclohexanedione and 8 ml of water was added 1.38 g (10 mmoles) of potassium carbonate, and then 2 ml of 40% aqueous solution of chloroacetaldehyde was added thereto. The resulting mixture was stirred at a room temperature for 45 hours. The reaction mixture was maintained at a pH of from 7.75 to 9.50 throughout the reaction. After completing the reaction, the obtained reaction mixture was treated and analyzed in the same manner as in Example 1. It was proved from the results of the analysis that 4-oxo-4,5,6,7-tetrahydrobenzofuran was produced in a 68% yield.

EXAMPLE 11

To a mixture of 80 ml of water and 20 ml of 40% aqueous solution of chloroacetaldehyde was added 10.0 g (119 mmoles) of sodium hydrogencarbonate while cooling with ice. To the resulting reaction mixture was added dropwise 90 ml of aqueous solution containing 11.2 g (100 mmoles) of 1,3-cyclohexanedione while cooling with ice at a rate of 0.4 ml/minute. The reaction mixture was maintained at a pH of from 9 to 6 throughout the reaction. After completing the dropping, the reaction mixture was stirred at a room temperature overnight. To the resulting reaction mixture was added about 100 ml of ethyl acetate, and then the reaction mixture was acidified (pH<1) with sulfuric acid and stirred for about one hour. The ethyl acetate layer was separated, washed with an aqueous solution of potassium carbonate, and dried on magnesium sulfate. After distilling away the ethyl acetate, the obtained residue was distilled under a reduced pressure to give 10.3 g (yield: 76%) of 4-oxo-4,5,6,7-tetrahydrobenzofuran being a colorless oily material (boiling point: 66° C./1 torr).

EXAMPLE 12

To a mixture of 10 ml of ethyl acetate, 2 ml of 40% aqueous solution of chloroacetaldehyde and about 3 ml of water was added 1.0 g (12 mmoles) of sodium hydrogencarbonate while cooling with ice, and then the resulting mixture was stirred. To the reaction mixture was added dropwise 5 ml of aqueous solution containing 1.12 g of 1,3-cyclohexanedione while cooling with ice at a rate of 0.05 ml/minute. The reaction mixture was maintained at a pH of from 6.2 to 8.7 throughout the reaction. After completing the dropping, the reaction mixture was stirred at a room temperature overnight, and then acidified with sulfuric acid. After stirring the mixture for one hour, the ethyl acetate layer was separated, washed with an aqueous solution of potassium carbonate for removing the unreacted 1,3-cyclohexanedione, and then dried on magnesium sulfate. After distilling away the solvent, the residue was applied to a column of silica gel and eluted with dichloromethane to give 1.09 g (yield: 80%) of 4-oxo-4,5,6,7-tetrahydrobenzofuran.

EXAMPLE 13

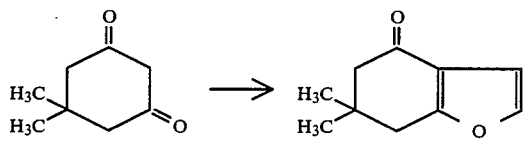

To a mixture of 24 ml of water and 6 ml of 40% aqueous solution of chloroacetaldehyde was added 0.7 g (8 mmoles) of sodium hydrogencarbonate while cooling with ice. To the reaction mixture were added dropwise 4.2 g (30 mmoles) of 5,5-dimethyl-1,3-cyclohexanedione and 40 ml of aqueous solution containing 2.3 g (27 mmoles) of sodium hydrogencarbonate while cooling with ice at a rate of 0.4 ml/minute. The reaction mixture was maintained at a pH of from 5.7 to 8.0 throughout the reaction. After completing the dropping, the reaction mixture was stirred at a room temperature overnight, and then treated in the same manner as in Example 1 to give 2.36 g (yield: 48.2%) of 4-oxo-6,6-dimethyl-4,5,6,7-tetrahydrobenzofuran being a colorless oily material (boiling point: 78° C./0.7 mmHg).

REFERENCE EXAMPLE

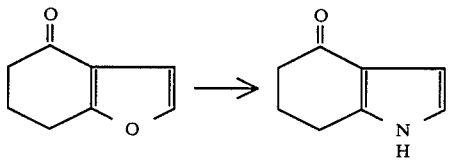

To a mixture of 3 ml of ethanol and 7 ml of 29% aqueous ammonia was added 1.0 g of 4-oxo-4,5,6,7-tetrahydrobenzofuran, and then the mixture was subjected to reaction in a sealed tube at 150° C. for 12 hours. After completing the reaction, the reaction mixture was concentrated. The resulting residue was applied to a column of silica gel and eluted with a mixed solvent of acetone and ethyl acetate to give 950 mg (yield: 96%) of 4-oxo-4,5,6,7-tetrahydroindole being a light yellowish crystal.

What we claim is:

1. A process for preparing 4-oxo-4,5,6,7-tetrahydrobenzofuran of the formula:

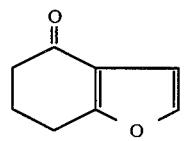

which comprises reacting 1,3-cyclohexanedione with a mixture of chloroacetaldehyde and a base selected from the group consisting of triethylamine, NaHCO₃, NaOH and K₂CO₃ or reacting chloroacetaldehyde with a mixture of 1,3-cyclohexanedione and said base while maintaining the resulting mixture at a pH of from 4 to 10 and treating the reaction mixture with an acid.

* * * * *